(12) United States Patent
Sun et al.

(10) Patent No.: US 11,330,824 B2
(45) Date of Patent: May 17, 2022

(54) MULTI-TEMPERATURE-REGION ICE-TEMPERATURE FRESH KEEPING STOREHOUSE AND FRESH KEEPING METHOD FOR BERGAMOT PEARS

(71) Applicant: SOUTH CHINA UNIVERSITY OF TECHNOLOGY, Guangzhou (CN)

(72) Inventors: Dawen Sun, Guangzhou (CN); Tingtiao Pan, Guangzhou (CN); Hongbin Pu, Guangzhou (CN); Zhiwei Zhu, Guangzhou (CN); Zhong Han, Guangzhou (CN)

(73) Assignee: SOUTH CHINA UNIVERSITY OF TECHNOLOGY, Gaungzhou (CN)

( * ) Notice: Subject to any disclaimer, the term of this patent is extended or adjusted under 35 U.S.C. 154(b) by 209 days.

(21) Appl. No.: 16/324,586

(22) PCT Filed: Nov. 23, 2017

(86) PCT No.: PCT/CN2017/112640
§ 371 (c)(1),
(2) Date: Feb. 11, 2019

(87) PCT Pub. No.: WO2018/095370
PCT Pub. Date: May 31, 2018

(65) Prior Publication Data
US 2019/0166860 A1 Jun. 6, 2019

(30) Foreign Application Priority Data
Nov. 24, 2016 (CN) .......................... 201611041797.5

(51) Int. Cl.
*A23B 7/04* (2006.01)
*G01N 33/02* (2006.01)
(Continued)

(52) U.S. Cl.
CPC ............ *A23B 7/0408* (2013.01); *F25D 13/04* (2013.01); *G01N 21/25* (2013.01); *G01N 33/025* (2013.01);
(Continued)

(58) Field of Classification Search
CPC .......... A23B 7/04; F25D 13/06; G01N 33/025
See application file for complete search history.

(56) References Cited

U.S. PATENT DOCUMENTS 2,103,925 A * 12/1937 Zarotschenzeff .... A23B 7/0441
426/639
5,873,254 A * 2/1999 Arav ........................ A01N 1/02
62/374
(Continued)

FOREIGN PATENT DOCUMENTS

CN 202522003 U 11/2012
CN 104567198 4/2015
(Continued)

*Primary Examiner* — Lionel Nouketcha
(74) *Attorney, Agent, or Firm* — JMB Davis Ben-David

(57) ABSTRACT

Disclosed herein is a multi-temperature-region ice-temperature fresh keeping storehouse and a fresh keeping method for bergamot pears that includes a precooling region, a feeding and discharging channel, a cooling region, an ice temperature detection device, a grading device, a conveyer belt control device, an automatic storage device, and a temperature rise and fall buffering channel. The cooling region includes four freezers, with temperatures ranging from 0° C.--3° C. The four freezers are connected level by level according to a temperature reduction rule. The present disclosure implements multi-temperature-region graded storage of bergamot pears according to the value of an ice point temperature of the bergamot pears, so that they are always stored close to the ice point temperature without freezing, thereby preventing freeze injury, and prolonging shelf life.

12 Claims, 1 Drawing Sheet

(51) Int. Cl.
*F25D 13/04* (2006.01)
*F25D 13/06* (2006.01)
*G01N 21/25* (2006.01)
*G06Q 10/08* (2012.01)

(52) U.S. Cl.
CPC .......... *A23V 2002/00* (2013.01); *F25D 13/06* (2013.01); *F25D 2500/00* (2013.01); *F25D 2700/00* (2013.01); *F25D 2700/121* (2013.01); *G06Q 10/087* (2013.01)

(56) References Cited

U.S. PATENT DOCUMENTS

2011/0030393 A1\* 2/2011 Hummrich .............. F25D 25/04
                                                                62/63
2017/0035070 A1\* 2/2017 Hastings .................. A23B 7/06

FOREIGN PATENT DOCUMENTS

| CN | 104920588 | 9/2015 |
| CN | 105910366 | 8/2016 |
| CN | 106472659 | 3/2017 |
| CN | 206413678 U | 8/2017 |
| JP | 2011078333 A | 4/2011 |

\* cited by examiner

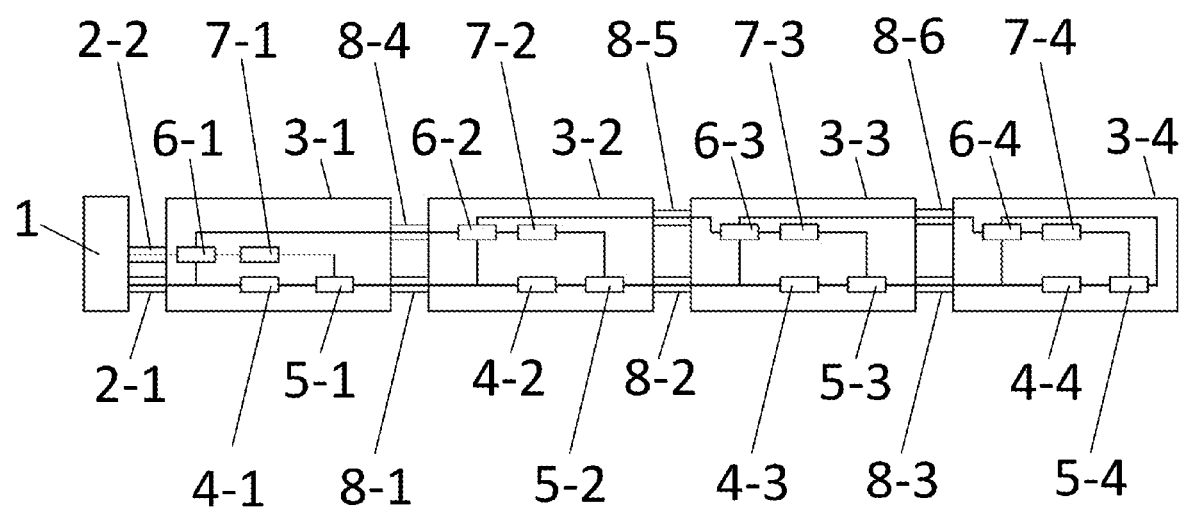

US 11,330,824 B2

MULTI-TEMPERATURE-REGION ICE-TEMPERATURE FRESH KEEPING STOREHOUSE AND FRESH KEEPING METHOD FOR BERGAMOT PEARS

CROSS-REFERENCE TO RELATED APPLICATIONS

This is the U.S. National Stage of International Application No. PCT/CN2017/112640 filed Nov. 23, 2017, which was published in Chinese under PCT Article 21(2), and which in turn claims the benefit of China Patent Application No. 201611041797.5, filed Nov. 24, 2016.

FIELD OF THE INVENTION

The present invention relates to the field of a fresh keeping storehouse and ice point temperature fresh keeping technology for fruits and vegetables, in particular to a multi-temperature-region ice point temperature fresh keeping storehouse and a fresh keeping method for bergamot pears.

BACKGROUND OF THE INVENTION

The bergamot pears produced in Ku'erle have thin peel, are juicy, sweet, fragrant and nutritious, and have good quality. However, they are not resistant to storage; after 15 days of storage at room temperature, their flesh begins to soften, and their peel begins to lose water and shrink, thus reducing the commodity value. Therefore, how to prolong the shelf life of bergamot pears more effectively and maintain their original quality and flavor is of great significance.

The existing fresh keeping methods for bergamot pears mainly include the traditional low-temperature refrigeration and modified atmosphere preservation, as well as the ice point temperature storage technology developed in recent years. Ice point temperature storage means storing fresh food within an unfrozen range from below 0° C. to above the ice point temperature, minimizing the respiratory rate of living body and inhibiting the growth of pathogenic microorganisms without destroying the cell structure of the stored food and causing no cold injury, so as to prolong the shelf life of the food. Ice point temperature storage has obvious advantages in maintaining the freshness and flavor of food, but it has strict requirements on storage temperature and requires a temperature close to the ice point temperature of food, because too low a temperature will directly cause freeze injury of food, while too high a temperature will not achieve the purpose of maximizing the shelf life of food.

Chinese invention patent application CN104567198A disclosed a design method and a cooling control method for a multi-warehouse isothermal freezer cooling system, and respectively calculated the cooling equipment load of n warehouses according to the existing thermal load calculation method for freezers; with this load applicable to the configuration of the cooling equipment of the n warehouses, the cooling equipment was configured by multiplication with a correction factor of 1.1 to 1.3 based on this load; full consideration was given to the influence of the season of the highest ambient temperature, the period of the maximum door opening number and the period of the maximum purchase volume on the cooling rate of the freezer, and a compression condensing unit was configured according to the cooling capacity of the cooling equipment of the largest warehouse. The method of this invention could greatly reduce the one-time investment in the cooling system as well as the investment in construction, power equipment and the like. It could reduce the volume of the cooling system of a large-scale freezer, the refrigerant filling amount, the safety hazard, and the one-time investment in refrigerant. This invention patent could provide a multi-warehouse freezer, and had obvious advantages in construction, power equipment investment and operating energy consumption, and the design method of the cooling system of this invention reduced safety hazards and improved environmental performance. However, the temperature set in the multiple warehouses of this invention was identical, which limited the fresh keeping effect.

Chinese invention patent application CN104482703A disclosed a multi-warehouse freezer with an integrated cooling system, which could perform cooling according to cooling requirements; this multi-warehouse freezer comprised a warehouse maintenance structure, an air cooler for the freezer, an air-cooled compression condensing unit, a transverse rail and a longitudinal rail; the warehouse maintenance structure was divided into a plurality of warehouses, each of which was provided in the front with an open-type insulated door; the air cooler for the freezer was connected with the air-cooled compression condensing unit to form an integrated cooling system, which was slidably connected with the transverse rail and the longitudinal rail to realize the multi-warehouse mobile cooling. The freezer of this invention had a plurality of warehouses sharing a cooling system, which greatly reduced the initial investment. The refrigerant filling amount was only the filling amount of one cooling system, the safety of the system was greatly improved, and energy-saving operation of the freezer and constant temperature in the freezer were achieved. Although this invention patent could provide a multi-warehouse freezer and also perform cooling according to the cooling requirements, it did not relate to the ice point temperature storage technology, and the storage temperature was not designed according to the gradient descent law, which easily led to cold injury, freeze injury and declined quality of fruits and vegetables, not achieving the purpose of preservation.

CONTENTS OF THE INVENTION

A purpose of the present invention is to provide a multi-temperature-region ice point temperature fresh keeping storehouse and a fresh keeping method for bergamot pears; before and during storage, the ice point temperature of bergamot pears is detected online, and the bergamot pears are graded and accordingly stored based on the detection results, with the storage temperature designed strictly according to the gradient descent law to ensure that the bergamot pears are always stored near the ice point temperature, such that the bergamot pears can be more effectively prevented from decaying, deteriorating and being frozen, and have a prolonged shelf life and a controlled cold injury rate below 1%.

Ice point temperature storage technology was first discovered and proposed by Dr. Yamane Shomei of Japan in the 1970s. Afterwards the ice point temperature technology has been widely used in Japan, and the corresponding ice point temperature cold chain system has been established. China introduced the concept of ice point temperature technology in the 1980s. The near-ice-point storage technology similar to the ice point temperature technology in principle has been applied to garlic, winter jujube, grape, chestnut and other agricultural products, but the application effect is not very satisfactory; this is mainly due to the fact that the ice point temperature of fruits and vegetables involved in the ice point temperature storage technology is not easy to determine, i.e., a slightly lower temperature will cause freeze injury to fruits and vegetables, which is not conducive to the long-term storage of fruits and vegetables, while a slightly higher temperature will not achieve the ideal fresh keeping effect; besides, the temperature in the technology is difficult to control.

The existing ice point temperature storage technology determines the ice point temperature mainly by using the accumulation of ice point data of fruits and vegetables as a reference range, or indirectly determines the ice point temperature by using the measurement results of traditional methods (such as an ice brine bath method). From a practical point of view, the ice point temperature determined by these methods not only is inaccurate, but also needs a long experimental period to determine, which is not conducive to rapid control.

The ice point temperature of bergamot pears varies greatly depending on their sugar degree, which is directly related to the variety, origin and maturity of bergamot pears and generally in the range of 10%-13%; the bergamot pears with a higher sugar degree usually have a lower ice point temperature due to their higher cell sap concentration, while the bergamot pears with a lower sugar degree usually have a higher ice point temperature. For example, bergamot pears of Ku'erle are a famous and special product in Xinjiang, and their production area is broad; in addition, the maturity of bergamot pears at the time of picking is also different. Therefore, the ice point temperature of the bergamot pears to be stored differs greatly. If the individual differences are not considered, it is unscientific to indirectly determine the ice point temperature of the bergamot pears to be stored by directly using the ice point data of bergamot pears or determining the ice point temperature of other bergamot pears by conventional methods. Besides, for different bergamot pears, their ice point temperature varies over a wide range. Therefore, if a certain value is selected in this large range to set the storage temperature, the storage temperature may be higher or lower, and the ice point temperature storage effect will not be obvious.

The multi-temperature-region ice point temperature fresh keeping storehouse for bergamot pears of the present invention is equipped with an on-line ice point temperature detection device, which can directly detect on-line the ice point temperature of all the bergamot pears that are about to enter the freezer, thereby solving the problem that it is unscientific to indirectly determine the ice point temperature of the bergamot pears. In particular, the present invention has found that the ice point temperature of different bergamot pears is distributed in the range of −3° C. to 0° C., and the design of freezers of four temperatures (0° C., −1° C., −2° C. and −3° C.) can achieve the graded storage of bergamot pears with different ice point temperatures, thus solving the problem of a higher or lower storage temperature and ensuring that bergamot pears are always stored near the ice point temperature. The four freezers are connected level by level according to a temperature reduction rule, which can ensure that the temperature of the bergamot pears with a lower ice point temperature can slowly drop to near the ice point temperature, so as to avoid the rapid decline of the quality of the bergamot pears caused by rapid cooling, with a significant effect of avoiding freeze injury while maximizing the shelf life. Compared with the cold injury rate of 34% of the fixed-temperature ice point temperature storage, the present invention has a cold injury rate of only 1%.

The purpose of the present invention is achieved by the following technical solution:

A multi-temperature-region ice point temperature fresh keeping storehouse for bergamot pears is provided, comprising a precooling region, a feeding and discharging channel, a cooling region, an ice point temperature detection device, a grading device, a conveyer belt control device, an automatic storage device, and a temperature rise and fall buffering channel; the cooling region comprises four freezers, which respectively are a first freezer in which the storage temperature is 0° C., a second freezer in which the storage temperature is −1° C., a third freezer in which the storage temperature is −2° C., and a fourth freezer in which the storage temperature is −3° C., with the four freezers connected level by level according to a temperature reduction rule; the precooling region is connected to the cooling region via the feeding and discharging channel; the ice point temperature detection device comprises a first ice point temperature detection device, a second ice point temperature detection device, a third ice point temperature detection device, and a fourth ice point temperature detection device; the grading device comprises a first grading device, a second grading device, a third grading device, and a fourth grading device; the conveyor belt control device comprises a first conveyor belt control device, a second conveyor belt control device, a third conveyor belt control device, and a fourth conveyor belt control device; the automatic storage device comprises a first automatic storage device, a second automatic storage device, a third automatic storage device, and a fourth automatic storage device; the temperature rise and fall buffering channel comprises a first temperature fall buffering channel, a second temperature fall buffering channel, a third temperature fall buffering channel, a first temperature rise buffering channel, a second temperature rise buffering channel, and a third temperature rise buffering channel;

the inlet of the first ice point temperature detection device is connected to the feeding channel via a conveyor belt, and the outlet of the first ice point temperature detection device is connected to the inlet of the first grading device via the conveyor belt; the outlet of the first grading device is connected to the first temperature fall buffering channel and the first automatic storage device via the conveyor belt; the first conveyor belt control device is connected to the inlets of the first automatic storage device, the first temperature rise buffering channel, the discharging channel and the first grading device via the conveyor belt; the inlet of the second ice point temperature detection device is connected to the outlet of the first grading device via the conveyor belt, and the outlet of the second ice point temperature detection device is connected to the inlet of the second grading device via the conveyor belt; the outlet of the second grading device is connected to the second temperature fall buffering channel and the second automatic storage device via the conveyor belt; the second conveyor belt control device is connected to the inlet of the second automatic storage device, the second temperature rise buffering channel, the first temperature rise buffering channel and the second grading device via the conveyor belt; the inlet of the third ice point temperature detection device is connected to the outlet of the second grading device via the conveyor belt, and the outlet of the third ice point temperature detection device is connected to the inlet of the third grading device via the conveyor belt; the outlet of the third grading device is connected to the third temperature fall buffering channel and the third automatic storage device via the conveyor belt; the third conveyor belt control device is connected to the inlet of the third automatic storage device, the third temperature rise buffering channel, the second temperature rise buffering channel and the third grading device via the conveyor belt; the inlet of the fourth ice point temperature detection device is connected to the outlet of the third grading device via the conveyor belt, and the outlet of the fourth ice point temperature detection device is connected to the inlet of the fourth grading device via the conveyor belt; the outlet of the fourth grading device is connected to the fourth automatic storage device via the conveyor belt; the fourth conveyor belt control device is connected to the inlets of the fourth automatic storage device and the fourth grading device, and the third temperature rise buffering channel via the conveyor belt.

In order to further achieve the purpose of the present invention, preferably, the cooling region adopts a freezer of Guangzhou Yuelian Fisheries Refrigeration Engineering Co., Ltd. at a working temperature from −3° C. to 0° C., and is used for storing bergamot pears of different ice point temperatures.

Preferably, the ice point temperature detection device adopts the GaiaSort push-scan hyperspectral imaging system of Sichuan Dualix Spectral Imaging Co., Ltd. for obtaining the spectral image of bergamot pears and realizing the rapid detection of the ice point temperature of bergamot pears.

Preferably, the grading device adopts a grader of Jiangsu Seagull Food Machinery Manufacturing Co., Ltd. for realizing the partition storage of bergamot pears according to the ice point temperature thereof.

Preferably, the automatic storage device adopts an automatic storage system of Taiwan Murata Machinery Co., Ltd. in a refrigerating/freezing environment for storage management of bergamot pears in different freezers.

Preferably, the conveyor belt control device adopts a food-grade base belt horizontal conveyor of Jiangsu Seagull Food Machinery Manufacturing Co., Ltd., and is used for conveying and dispatching bergamot pears in different freezers.

Preferably, the precooling region adopts a freezer of Guangzhou Yuelian Fisheries Refrigeration Engineering Co., Ltd. at a working temperature of 0° C., and is used for centrally precooling bergamot pears and reducing the temperature fluctuation of the first cooling region, the second cooling region, the third cooling region and the fourth cooling region.

The fresh keeping method of the multi-temperature-region ice point temperature fresh keeping storehouse for bergamot pears comprises the following steps:

S0: establishing a predictive model;

S0-1: harvesting samples of bergamot pears of different origins and different maturity, using a temperature detection device to obtain the spectral imaging information of the bergamot pear samples, and determining the ice point temperature of the same by an ice brine bath method;

S0-2: obtaining average reflection spectrum values corresponding to characteristic wavelengths of 434 nm, 531 nm, 689 nm, 819 nm and 996 nm of the bergamot pear spectrum;

S0-3: combining the ice point temperature obtained in Step S0-1 with the average reflection spectrum values corresponding to the characteristic wavelengths obtained in Step S0-2, and establishing a predictive model equation of the ice point temperature of bergamot pears as follows by a partial least squares method: $Y_b = -1.261 - 0.022X_{434} + 0.056X_{531} - 0.061X_{689} - 0.079X_{819} + 0.072X_{996}$, wherein $Y_b$ is a predictive result of the ice point temperature, and $X_i$ is an average reflection spectrum value corresponding to the wavelength of i;

S1: judging whether there is a bergamot pear entering the fresh keeping storehouse, if there is, then proceeding to S2;

S2: the bergamot pears are precooled in the precooling region; after the precooling is finished, the bergamot pears are transported via the feeding channel to the first ice point temperature detection device, which acquires the spectral imaging information of the bergamot pears; the ice point temperature of the bergamot pears to be stored is quickly predicted based on the predictive model established in Step S0, and transmitted to the first grading device via the communication line; the first grading device determines the storage process of the bergamot pears according to the ice point temperature of the bergamot pears: if the freezing point of the bergamot pears is above or at −1° C., the first grading device transports the bergamot pears via the conveyor belt to the first automatic storage device, which completes the automatic storage of the bergamot pears; if the ice point temperature of the bergamot pears is below −1° C., the first grading device transports the bergamot pears to the second freezer via the first temperature fall buffering channel, and then the process proceeds to Step S3;

S3: the bergamot pears, after being cooled by the first temperature fall buffering channel, are transported to the second ice point temperature detection device, which obtains the spectral imaging information of the bergamot pears; the ice point temperature of the bergamot pears is quickly predicted based on the predictive model established in Step S0, and transmitted to the second grading device via the communication line; the second grading device determines the storage process of the bergamot pears according to the ice point temperature of the bergamot pears: if the freezing point of the bergamot pears is above or at −2° C., the second grading device transports the bergamot pears via the conveyor belt to the second automatic storage device, which completes the automatic storage of the bergamot pears; if the ice point temperature of the bergamot pears is below −2° C., the second grading device transports the bergamot pears to the third freezer via the second temperature fall buffering channel, and then the process proceeds to Step S4;

S4: the bergamot pears, after being cooled by the second temperature fall buffering channel, are transported to the third ice point temperature detection device, which obtains the spectral imaging information of the bergamot pears; the ice point temperature of the bergamot pears is quickly predicted based on the predictive model established in Step S0, and transmitted to the third grading device via the communication line; the third grading device determines the storage process of the bergamot pears according to the ice point temperature of the bergamot pears: if the freezing point of the bergamot pears is above or at −3° C., the third grading device transports the bergamot pears via the conveyor belt to the third automatic storage device, which completes the automatic storage of the bergamot pears; if the ice point temperature of the bergamot pears is below −3° C., the third grading device transports the bergamot pears to the fourth freezer via the third temperature fall buffering channel, and then the process proceeds to Step S5;

S5: the bergamot pears, after being cooled by the third temperature fall buffering channel, are transported to the fourth ice point temperature detection device, which obtains the spectral imaging information of the bergamot pears; the ice point temperature of the bergamot pears is quickly predicted based on the predictive model established in Step S0, and transmitted to the fourth grading device via the communication line; the fourth grading device determines the storage process of the bergamot pears according to the ice point temperature of the bergamot pears: if the freezing point of the bergamot pears is below −3° C., the fourth grading device transports the bergamot pears via the conveyor belt to the fourth automatic storage device, which completes the automatic storage of the bergamot pears; if the ice point temperature of the bergamot pears is above or at −3° C., the fourth grading device transports the bergamot pears to the fourth conveyor belt control device via the conveyor belt, and then the process proceeds to Step S6;

S6: the fourth conveyor belt control device, according to the ice point temperature information of the bergamot pears, transports the bergamot pears to the third conveyor belt control device via the third temperature rise buffering channel; if the ice point temperature of the bergamot pears is below −2° C., the bergamot pears are transported to the third automatic storage device, otherwise to the second conveyor belt control device via the second temperature rise buffering channel by the third conveyor belt control device according to the ice point temperature of the bergamot pears; if the ice point temperature of the bergamot pears is below −1° C., the bergamot pears are transported to the second automatic storage device, otherwise to the first conveyor belt control device via the first temperature rise buffering channel by the second conveyor belt control device according to the ice point temperature of the bergamot pears, with the first conveyor belt control device transporting the bergamot pears to the first automatic storage device.

The present invention has the following advantages and benefits compared to the prior art:

(1) The multi-temperature-region ice point temperature fresh keeping storehouse of the present invention has a plurality of freezers, which can meet different temperature requirements of different stored items. The temperature of different freezers is strictly controlled for achieving gradient descent preservation. The purpose for this is to ensure that the bergamot pears with a relatively high ice point temperature are first screened for storage, while the bergamot pears with a lower ice point temperature need to be precooled to near the ice point temperature and then stored, so as to avoid the effect of rapid cooling on the quality of bergamot pears.

(2) The rapid spectrum detection of the ice point temperature of bergamot pears of the present invention realizes the partition storage of bergamot pears according to the ice point temperature. For fruits and vegetables with a wide range of ice point temperature, graded storage can ensure that the storage temperature set in the ice point temperature storage process is closer to the ice point temperature of fruits and vegetables, preventing the storage temperature from being too high or too low, and better maintaining the original quality of fruits and vegetables. With cold injury as the most likely problem of ice point temperature storage, the present invention keeps the cold injury rate of bergamot pears below 1%, which is significantly lower than the cold injury rate of the existing ice point temperature storage technology.

(3) The multi-temperature-region ice point temperature fresh keeping storehouse of the present invention is provided with a precooling region and a buffering channel, thereby effectively avoiding frequent temperature fluctuation of the freezers.

(4) The multi-temperature-region ice point temperature fresh keeping storehouse of the present invention can simultaneously realize the determination and control of the ice point temperature of bergamot pears. An ice point temperature detection device is arranged in the fresh keeping storehouse, and the ice point temperature can be determined according to the detection result. In addition, in the storage process, the storage region can be continuously adjusted according to the change of the ice point temperature of bergamot pears, so as to achieve precise control of the storage and preservation of bergamot pears.

BRIEF DESCRIPTION OF THE DRAWINGS

FIG. 1 is a structural schematic view of a multi-temperature-region ice point temperature fresh keeping storehouse and a fresh keeping method for bergamot pears according to the present invention.

DETAILED DESCRIPTION OF THE EMBODIMENTS

In order to better understand the present invention, the present invention will be further described below in conjunction with the drawings and examples; however, the embodiments of the present invention are not limited thereto.

Example 1

A multi-temperature-region ice point temperature fresh keeping storehouse for bergamot pears is provided, comprising a precooling region 1, a feeding and discharging channel, a cooling region, an ice point temperature detection device, a grading device, a conveyer belt control device, an automatic storage device, and a temperature rise and fall buffering channel; the precooling region 1 is connected to the cooling region via the feeding and discharging channel; the feeding and discharging channel comprises a feeding channel 2-1 and a discharging channel 2-2; the cooling region comprises four freezers, which respectively are a first freezer 3-1 in which the storage temperature is 0° C., a second freezer 3-2 in which the storage temperature is −1° C., a third freezer 3-3 in which the storage temperature is −2° C., and a fourth freezer 3-4 in which the storage temperature is −3° C., with the four freezers connected level by level according to a temperature reduction rule; the ice point temperature detection device comprises a first ice point temperature detection device 4-1, a second ice point temperature detection device 4-2, a third ice point temperature detection device 4-3, and a fourth ice point temperature detection device 4-4; the grading device comprises a first grading device 5-1, a second grading device 5-2, a third grading device 5-3, and a fourth grading device 5-4; the conveyor belt control device comprises a first conveyor belt control device 6-1, a second conveyor belt control device 6-2, a third conveyor belt control device 6-3, and a fourth conveyor belt control device 6-4; the automatic storage device comprises a first automatic storage device 7-1, a second automatic storage device 7-2, a third automatic storage device 7-3, and a fourth automatic storage device 7-4; the temperature rise and fall buffering channel comprises a first temperature fall buffering channel 8-1, a second temperature fall buffering channel 8-2, a third temperature fall buffering channel 8-3, a first temperature rise buffering channel 8-4, a second temperature rise buffering channel 8-5, and a third temperature rise buffering channel 8-6; the inlet of the first ice point temperature detection device 4-1 is connected to the feeding channel 2-1 via a conveyor belt, and the outlet of the first ice point temperature detection device 4-1 is connected to the inlet of the first grading device 5-1 via the conveyor belt; the outlet of the first grading device 5-1 is connected to the first temperature fall buffering channel 8-1 and the first automatic storage device 7-1 via the conveyor belt; the first conveyor belt control device 6-1 is connected to the inlets of the first automatic storage device 7-1, the first temperature rise buffering channel 8-4, the discharging channel 2-2 and the first ice point temperature detection device 4-1 via the conveyor belt; the inlet of the second ice point temperature detection device 4-2 is connected to the outlet of the first grading device 5-1 via the conveyor belt, and the outlet of the second ice point temperature detection device 4-2 is connected to the inlet of the second grading device 5-2 via the conveyor belt; the outlet of the second grading device 5-2 is connected to the second temperature fall buffering channel 8-2 and the second automatic storage device 7-2 via the conveyor belt; the second conveyor belt control device 6-2 is connected to the second automatic storage device 7-2, the second temperature rise buffering channel 8-5, the first temperature rise buffering channel 8-1 and the second grading device 6-3 via the conveyor belt; the inlet of the third ice point temperature detection device 4-3 is connected to the outlet of the second grading device 5-2 via the conveyor belt, and the outlet of the third ice point temperature detection device 4-3 is connected to the inlet of the third grading device 5-3 via the conveyor belt; the outlet of the third grading device 5-3 is connected to the third temperature fall buffering channel 8-3 and the third automatic storage device 7-3 via the conveyor belt; the third conveyor belt control device 6-3 is connected to the third automatic storage device 7-3, the third temperature rise buffering channel 8-6, the second temperature rise buffering channel 8-5 and the third automatic storage device 7-3 via the conveyor belt; the inlet of the fourth ice point temperature detection device 4-4 is connected to the outlet of the third grading device 5-3 via the conveyor belt, and the outlet of the fourth ice point temperature detection device 4-4 is connected to the inlet of the fourth grading device 5-4 via the conveyor belt; the outlet of the fourth grading device 5-4 is connected to the fourth automatic storage device 7-4 via the conveyor belt; the fourth conveyor belt control device 6-4 is connected to the inlets of the fourth automatic storage device 7-4 and the fourth grading device 5-4, and the third temperature rise buffering channel 8-6 via the conveyor belt; the conveyor belt control device is connected to a controller of the automatic storage device, the grading device and the ice point temperature detection device via a communication line.

Preferably, the precooling region 1 uses a freezer of Guangzhou Yuelian Fisheries Refrigeration Engineering Co., Ltd. at a working temperature from −3° C. to 0° C., and is used for storing bergamot pears of different ice point temperatures.

Preferably, the ice point temperature detection device adopts the GaiaSort push-scan hyperspectral imaging system of Sichuan Dualix Spectral Imaging Co., Ltd. for obtaining the spectral image of bergamot pears and realizing the rapid detection of the ice point temperature of bergamot pears.

Preferably, the grading device adopts a grader of Jiangsu Seagull Food Machinery Manufacturing Co., Ltd. for realizing the partition storage of bergamot pears according to the ice point temperature thereof.

Preferably, the automatic storage device adopts an automatic storage system of Taiwan Murata Machinery Co., Ltd. in a refrigerating/freezing environment for storage of bergamot pears in different freezers.

Preferably, the conveyor belt control device adopts a food-grade base belt horizontal conveyor of Jiangsu Seagull Food Machinery Manufacturing Co., Ltd., and is used for conveying and dispatching bergamot pears in different freezers.

The fresh keeping method of the multi-temperature-region ice point temperature fresh keeping storehouse for bergamot pears according to this example comprises the following steps:

S0: establishing a predictive model;

S0-1: harvesting samples of bergamot pears of different origins and different maturity, using a temperature detection device to obtain the spectral imaging information of the bergamot pear samples, and determining the ice point temperature of these samples by an ice brine bath method;

S0-2: preprocessing the spectral information of the samples, i.e., obtaining average reflection spectrum values corresponding to characteristic wavelengths of 434 nm, 531 nm, 689 nm, 819 nm and 996 nm of the bergamot pear samples;

S0-3: combining the ice point temperature obtained in Step S0-1 with the average reflection spectrum values corresponding to the characteristic wavelengths obtained in Step S0-2, and establishing a predictive model equation of the ice point temperature of bergamot pears as follows by a partial least squares method: $Y_b = -1.261 - 0.022X_{434} + 0.056X_{531} - 0.061X_{689} - 0.079X_{819} + 0.072X_{996}$, wherein $Y_b$ is a predictive result of the ice point temperature, and $X_i$ is an average reflection spectrum value corresponding to the wavelength of i;

S1: judging whether there is a bergamot pear entering the fresh keeping storehouse, if there is, then proceeding to S2;

S2: the bergamot pears are precooled in the precooling region; after the precooling is finished, the bergamot pears are transported via the feeding channel to the first ice point temperature detection device, which acquires the spectral imaging information of the bergamot pears; the ice point temperature of the bergamot pears to be stored is quickly predicted based on the predictive model established in Step S0, and transmitted to the first grading device via the communication line; the first grading device determines the storage process of the bergamot pears according to the ice point temperature of the bergamot pears: if the freezing point of the bergamot pears is above or at −1° C., the first grading device transports the bergamot pears via the conveyor belt to the first automatic storage device, which completes the automatic storage of the bergamot pears; if the ice point temperature of the bergamot pears is below −1° C., the first grading device transports the bergamot pears to the second freezer via the first temperature fall buffering channel, and then the process proceeds to Step S3;

S3: the bergamot pears, after being cooled by the first temperature fall buffering channel, are transported to the second ice point temperature detection device, which obtains the spectral imaging information of the bergamot pears; the ice point temperature of the bergamot pears is quickly predicted based on the predictive model established in Step S0, and transmitted to the second grading device via the communication line; the second grading device determines the storage process of the bergamot pears according to the ice point temperature of the bergamot pears: if the freezing point of the bergamot pears is above or at −2° C., the second grading device transports the bergamot pears via the conveyor belt to the second automatic storage device, which completes the automatic storage of the bergamot pears; if the ice point temperature of the bergamot pears is below −2° C., the second grading device transports the bergamot pears to the third freezer via the second temperature fall buffering channel, and then the process proceeds to Step S4;

S4: the bergamot pears, after being cooled by the second temperature fall buffering channel, are transported to the third ice point temperature detection device, which obtains the spectral imaging information of the bergamot pears; the ice point temperature of the bergamot pears is quickly predicted based on the predictive model established in Step S0, and transmitted to the third grading device via the communication line; the third grading device determines the storage process of the bergamot pears according to the ice point temperature of the bergamot pears: if the freezing point of the bergamot pears is above or at −3° C., the third grading device transports the bergamot pears via the conveyor belt to the third automatic storage device, which completes the automatic storage of the bergamot pears; if the ice point temperature of the bergamot pears is below −3° C., the third grading device transports the bergamot pears to the fourth freezer via the third temperature fall buffering channel, and then the process proceeds to Step S5;

S5: the bergamot pears, after being cooled by the third temperature fall buffering channel, are transported to the fourth ice point temperature detection device, which obtains the spectral imaging information of the bergamot pears; the ice point temperature of the bergamot pears is quickly predicted based on the predictive model established in Step S0, and transmitted to the fourth grading device via the communication line; the fourth grading device determines the storage process of the bergamot pears according to the ice point temperature of the bergamot pears: if the freezing point of the bergamot pears is below −3° C., the fourth grading device transports the bergamot pears via the conveyor belt to the fourth automatic storage device, which completes the automatic storage of the bergamot pears; if the ice point temperature of the bergamot pears is above or at −3° C., the fourth grading device transports the bergamot pears to the fourth conveyor belt control device via the conveyor belt, and then the process proceeds to Step S6;

S6: the fourth conveyor belt control device, according to the ice point temperature information of the bergamot pears, transports the bergamot pears to the third conveyor belt control device via the third temperature rise buffering channel; if the ice point temperature of the bergamot pears is below −2° C., the bergamot pears are transported to the third automatic storage device, otherwise to the second conveyor belt control device via the second temperature rise buffering channel by the third conveyor belt control device according to the ice point temperature of the bergamot pears; if the ice point temperature of the bergamot pears is below −1° C., the bergamot pears are transported to the second automatic storage device, otherwise to the first conveyor belt control device via the first temperature rise buffering channel by the second conveyor belt control device according to the ice point temperature of the bergamot pears, with the first conveyor belt control device transporting the bergamot pears to the first automatic storage device.

Effects of different fresh keeping methods on the quality of bergamot pears Bergamot pears of Ku'erle with 80% maturity (having smooth surface and green-yellow peel, and being slightly reddish on the sunny side) were picked, packed (the fruits are wrapped in copy paper and then putted in a net bag), encased, and then shipped back to a freezer of the laboratory the next day; 400 fruits that had no pests and diseases, neat fruit shape, basically the same size and color, and no epidermal injury were randomly divided into 4 groups, with 100 in each group; the 4 groups of bergamot pears were treated for 80 days according to different fresh keeping methods (taking the first group as the control group), and then placed at room temperature (about 25° C.) for 2 days; and then the decay rate, cold injury rate, weight loss rate, peel color (brightness), quality and hardness of flesh, sugar degree and titrable acidity of the 4 groups of bergamot pears were determined, respectively. The different fresh keeping methods were as follows: Group 1, natural storage; Group 2, low temperature refrigeration (temperature: 4° C.; humidity: 90% to 95%); Group 3, ice point temperature storage (multiple temperature regions at a temperature of 0° C., −1° C., −2° C. and −3° C., respectively), performed according to Step S1 to Step S6; Group 4, ice point temperature storage (at a fixed temperature of −2° C.); after Step S1 to Step S6, the bergamot pears in all of the automatic storage devices were moved to the third automatic storage device 7-3. The measurement results were shown in Table 1.

TABLE 1

Effects of different fresh keeping methods on the quality of bergamot pears

| Group | Fresh keeping method | Rotting rate/% | Cold injury rate/% | Weight loss rate/% | Peel color (L) | Flesh quality | | |
|---|---|---|---|---|---|---|---|---|
| | | | | | | Hardness/N | Sugar degree/% | TA content/% |
| 1 | Natural storage | 29 | 0 | 5.89 | 52.86 | 10.25 | 12.72 | 0.059 |
| 2 | Low temperature refrigeration | 3 | 0 | 1.83 | 58.47 | 10.88 | 12.26 | 0.068 |
| 3 | Ice temperature storage (multiple temperature regions) | 0 | 1 | 0.81 | 62.78 | 11.19 | 12.11 | 0.078 |
| 4 | Ice temperature storage (fixed temperature) | 0 | 34 | 0.84 | 59.65 | 11.06 | 12.14 | 0.074 |

Note:
Fruits that had decayed and had cold injury were not counted.

As shown in Table 1, compared with the low temperature refrigeration, the ice point temperature storage can avoid the decay of bergamot pears; besides, the weight loss rate by the ice point temperature storage is below 1%, which is significantly lower than the weight loss rate by the low temperature refrigeration (1.83%), indicating that the ice point temperature storage can better retain the moisture of bergamot pears; in addition, the ice point temperature storage can delay the decrease of the hardness and titrable acidity of bergamot pears, and can also effectively delay the increase of the sugar degree of bergamot pears; in terms of maintaining the brightness of bergamot pears, the effect of the ice point temperature storage (especially multi-temperature-region ice point temperature storage) is also better than that of the low temperature refrigeration. In short, whether it is seen from the external quality of the stored food or analyzed from the internal quality of the same, the ice point temperature storage has a better fresh keeping effect, and can better maintain the original quality of bergamot pears. In terms of the ice point temperature storage, the effect of multi-temperature-region ice point temperature storage of the present invention is better than that of the fixed-temperature ice point temperature storage; the most noteworthy is that the multi-temperature-region ice point temperature storage can almost avoid the cold injury of bergamot pears, because all the storage temperatures set by the multi-temperature-region ice point temperature storage are close to the ice point temperature, while the storage temperature set by the fixed-temperature ice point temperature storage is a certain value within a range, and the bergamot pears with an ice point temperature higher than this value may be cold-injured in the long-term storage process. The multi-temperature-region ice point temperature storage of the present invention better preserves the peel color of bergamot pears than the fixed-temperature ice point temperature storage; this is possibly because the fixed-temperature ice point temperature storage may cause frostbite of some bergamot pears and increase the possibility of contact between the enzyme and the substrate, which eventually leads to some enzymatic reactions to cause changes in the peel color. In summary, the multi-temperature-region ice point temperature storage is the most ideal method for storage and preservation of bergamot pears. Compared with the cold injury rate of 34% of the fixed-temperature ice point temperature storage, the present invention has only a cold injury rate of 1%, having a very significant improvement effect. In order to achieve a better fresh keeping effect, the ice point temperature storage technology tends to set the storage temperature to be very low, making the cold injury be the most important problem of the existing ice point temperature storage technology. The present invention greatly reduces the cold injury rate while achieving the best fresh keeping effect.

The embodiments of the present invention are not limited to the above examples, and any other alterations, modifications, substitutions, combinations and simplifications made without departing from the spirit and principle of the present invention should all be equivalent replacements and included in the scope of protection of the present invention.

The invention claimed is:

1. A multi-temperature-region storehouse for bergamot pears, comprising:
   a precooling region;
   a feeding and discharging channel;
   a cooling region;
   an ice point temperature detection device comprising an imaging system for obtaining spectral imaging information of each of the bergamot pears to detect an ice point temperature of said bergamot pear;
   a grading device comprising a grader for realizing partition storage of bergamot pears according to the ice point temperature of said bergamot pear;
   a conveyor belt control device comprising a conveyor for conveying and dispatching the bergamot pears;
   an automatic storage device comprising an automatic storage system for storage of the bergamot pears; and
   a temperature rise and fall buffering channel;
   wherein the cooling region comprises more than one freezer with different temperatures and wherein the more than one freezer are connected to each other according to a temperature reduction rule;
   wherein each of the bergamot pears is stored at the freezer having a temperature closest to the ice point temperature of said bergamot pear; and
   wherein the precooling region is connected to the cooling region via the feeding and discharging channel.

2. The storehouse of claim 1, wherein the cooling region comprises four freezers, each with a different temperature.

3. The storehouse of claim 2, wherein the four freezers are a first freezer in which the storage temperature is 0° C., a second freezer in which the storage temperature is −1° C., a third freezer in which the storage temperature is −2° C., and a fourth freezer in which the storage temperature is −3° C.

4. The storehouse of claim 3, wherein the ice point temperature detection device comprises a first, a second, a third, and a fourth ice point temperature detection device;
   wherein the grading device comprises a first, a second, a third, and a fourth grading devices;
   wherein the conveyor belt control device comprises a first, a second, a third, and a fourth conveyor belt control device;
   wherein the automatic storage device comprises a first, a second, a third, and a fourth automatic storage device; and wherein the temperature rise and fall buffering channel comprises a first, a second, and a third temperature fall buffering channel, and a first, a second, and a third temperature rise buffering channel.

5. The storehouse of claim 4, wherein an inlet of the first ice point temperature detection device is connected to a feeding channel via a conveyor belt, and an outlet of the first ice point temperature detection device is connected to an inlet of the first grading device via the conveyor belt;
   the outlet of the first grading device is connected to the first temperature fall buffering channel and the first automatic storage device via the conveyor belt;
   the first conveyor belt control device is connected to an inlets of the first automatic storage device, the first temperature rise buffering channel, the discharging channel and the first grading device via the conveyor belt;
   an inlet of the second ice point temperature detection device is connected to the outlet of the first grading device via the conveyor belt, and an outlet of the second ice point temperature detection device is connected to an inlet of the second grading device via the conveyor belt;
   an outlet of the second grading device is connected to the second temperature fall buffering channel and the second automatic storage device via the conveyor belt;
   the second conveyor belt control device is connected to an inlet of the second automatic storage device, the second temperature rise buffering channel, the first temperature rise buffering channel and the second grading device via the conveyor belt;
   an inlet of the third ice point temperature detection device is connected to an outlet of the second grading device via the conveyor belt, and an outlet of the third ice point temperature detection device is connected to an inlet of the third grading device via the conveyor belt;

an outlet of the third grading device is connected to the third temperature fall buffering channel and the third automatic storage device via the conveyor belt;

the third conveyor belt control device is connected to an inlet of the third automatic storage device, the third temperature rise buffering channel, the second temperature rise buffering channel and the third grading device via the conveyor belt;

an inlet of the fourth ice point temperature detection device is connected to the outlet of the third grading device via the conveyor belt, and an outlet of the fourth ice point temperature detection device is connected to an inlet of the fourth grading device via the conveyor belt;

an outlet of the fourth grading device is connected to the fourth automatic storage device via the conveyor belt;

the fourth conveyor belt control device is connected to an inlets of the fourth automatic storage device and the fourth grading device, and the third temperature rise buffering channel via the conveyor belt.

6. The storehouse according to claim 3, wherein the precooling region comprises a freezer at 0° C.

7. The storehouse according to claim 3, wherein the cooling region comprises a freezer.

8. The storehouse according to claim 3, wherein the imaging system comprises a push-scan hyperspectral imaging system.

9. The storehouse according to claim 3, wherein the automatic storage system is in a refrigerated/frozen environment.

10. The storehouse according to claim 3, wherein the conveyor comprises a food-grade base belt horizontal conveyor.

11. The storehouse according to claim 3, wherein the conveyor belt control device is connected to a controller of the automatic storage device, the grading device and the ice point temperature detection device via a communication line.

12. A method for storing bergamot pears comprising:

S0: establishing a predictive model;

S0-1: harvesting samples of bergamot pears of different origins and different maturity, using a temperature detection device to obtain spectral imaging information of the bergamot pear samples, and determining a freezing point temperature of the same by an ice brine bath method;

S0-2: obtaining average reflection spectrum values corresponding to characteristic wavelengths of 434 nm, 531 nm, 689 nm, 819 nm and 996 nm of the bergamot pear samples;

S0-3: combining the freezing point temperature obtained in Step S0-1 with the average reflection spectrum values corresponding to the characteristic wavelengths obtained in Step S0-2, and establishing a predictive model equation by a partial least squares method: $Y_b = -1.261 - 0.022 \times 434 + 0.056 \times 531 - 0.061 \times 689 - 0.079 \times 819 + 0.072 \times 996$, wherein $Y_b$ is a predictive result of the freezing point temperature, and $X_i$ is an average reflection spectrum value corresponding to the wavelength of i;

S1: judging whether there is a bergamot pear entering a storehouse, if there is, then proceeding to S2;

S2: precooling the bergamot pears in a precooling region; after the precooling is finished, transporting the bergamot pears via a feeding channel to a first ice point temperature detection device, acquiring the spectral imaging information of the bergamot pears via the first ice point temperature detection device; predicting the freezing point temperature of the bergamot pears to be stored based on the predictive model established in Step S0, and transmitting to a first grading device via a communication line; determining a storage process of the bergamot pears by the first grading device according to the freezing point temperature of the bergamot pears: if the freezing point temperature of the bergamot pears is above or at −1° C., transporting the bergamot pears on the first grading device via a conveyor belt to a first automatic storage device, and completing automatic storage of the bergamot pears; if the freezing point temperature of the bergamot pears is below −1° C., transporting the bergamot pears on the first grading device to a second freezer via a first temperature fall buffering channel, and then proceeding to Step S3;

S3: after cooling the bergamot pears by the first temperature fall buffering channel, transporting them to a second ice point temperature detection device, and obtaining the spectral imaging information of the bergamot pears at the second ice point temperature detection device; predicting the freezing point temperature of the bergamot pears based on the predictive model established in Step S0, and transmitting to a second grading device via the communication line; at the second grading device determining the storage process of the bergamot pears according to the freezing point temperature of the bergamot pears: if the freezing point temperature of the bergamot pears is above or at −2° C., transporting the bergamot pears on the second grading device via the conveyor belt to a second automatic storage device, and completing the automatic storage of the bergamot pears; if the freezing point temperature of the bergamot pears is below −2° C., transporting the bergamot pears on the second grading device to a third freezer via a second temperature fall buffering channel, and then proceeding to Step S4;

S4: after cooling the bergamot pears, by the second temperature fall buffering channel, transporting them to a third ice point temperature detection device, and obtaining the spectral imaging information of the bergamot pears at the third ice point temperature detection device; predicting the freezing point temperature of the bergamot pears based on the predictive model established in Step S0, and transmitting to a third grading device via the communication line; determining by the third grading device the storage process of the bergamot pears according to the freezing point temperature of the bergamot pears: if the freezing point temperature of the bergamot pears is above or at −3° C., transporting by the third grading device the bergamot pears via the conveyor belt to a third automatic storage device, and completing the automatic storage of the bergamot pears; if the freezing point temperature of the bergamot pears is below −3° C., transporting by the third grading device the bergamot pears to a fourth freezer via a third temperature fall buffering channel, and proceeding to Step S5;

S5: cooling the bergamot pears by the third temperature fall buffering channel, transporting to a fourth ice point temperature detection device, and obtaining the spectral imaging information of the bergamot pears by the fourth ice point temperature detection device; predicting the freezing point temperature of the bergamot pears based on the predictive model established in Step S0, and transmitting to a fourth grading device via the communication line; determining by the fourth grading device, the storage process of the bergamot pears according to the freezing point temperature of the bergamot pears: if the freezing point temperature of the bergamot pears is below −3° C., transporting the bergamot pears by the fourth grading device via the conveyor belt to a fourth automatic storage device, completing the automatic storage of the bergamot pears; if the freezing point temperature of the bergamot pears is above or at −3° C., transporting the bergamot pears by the fourth grading device to a fourth conveyor belt control device via the conveyor belt, and proceeding to Step S6;

S6: transporting the bergamot pears via the fourth conveyor belt control device, according to the freezing point temperature information of the bergamot pears, to the third conveyor belt control device via a third temperature rise buffering channel; if the freezing point temperature of the bergamot pears is below −2° C., transporting the bergamot pears to the third automatic storage device, otherwise to the second conveyor belt control device via a second temperature rise buffering channel by the third conveyor belt control device according to the freezing point temperature of the bergamot pears; if the freezing point temperature of the bergamot pears is below −1° C., transporting the bergamot pears to the second automatic storage device, otherwise to the first conveyor belt control device via a first temperature rise buffering channel by the second conveyor belt control device according to the freezing point temperature of the bergamot pears, with the first conveyor belt control device transporting the bergamot pears to the first automatic storage device.

* * * * *